United States Patent [19]

Bostwick et al.

[11] Patent Number: 4,895,804
[45] Date of Patent: * Jan. 23, 1990

[54] BOVINE ANTIGEN GLYCOPROTEIN, RELATED ANTIBODY, AND USE IN DETECTION OF PREGNANCY IN CATTLE

[75] Inventors: Eileen F. Bostwick, St. Paul; Alan G. Hunter, Roseville, both of Minn.

[73] Assignee: University of Minnesota, St. Paul, Minn.

[*] Notice: The portion of the term of this patent subsequent to Jul. 5, 2005 has been disclaimed.

[21] Appl. No.: 88,346

[22] Filed: Aug. 24, 1987

Related U.S. Application Data

[63] Continuation-in-part of Ser. No. 628,571, Jul. 6, 1984, Pat. No. 4,755,460, and a continuation-in-part of Ser. No. 752,510, Jul. 8, 1985, abandoned.

[51] Int. Cl.$^4$ .................................. G01N 33/577
[52] U.S. Cl. ........................... 435/240.27; 422/61; 435/172.2; 435/810; 435/7; 436/510; 436/543; 436/548; 436/814; 436/828; 530/350; 530/387; 530/395; 530/403; 530/412; 530/416; 530/418; 530/427; 935/110
[58] Field of Search ............... 435/7, 172.2, 810, 110; 436/510, 543, 548, 814, 828; 530/350, 387, 395, 403, 412, 416, 418, 427, 850; 422/61

[56] References Cited

U.S. PATENT DOCUMENTS

4,065,445 12/1977 Bohn et al.
4,191,533 3/1980 Bohn et al.
4,217,339 8/1980 Bohn et al.
4,302,385 11/1981 Bohn et al.
4,444,879 4/1984 Foster et al.
4,489,166 12/1984 Joshi.
4,554,256 11/1985 Sasser et al.

FOREIGN PATENT DOCUMENTS

1492689 11/1977 United Kingdom.

OTHER PUBLICATIONS

Bostwick et al., (1983), J. Anim. Sci. 57 (suppl. 1), p. 320, Abstract 457.
Butler et al., (1980), J. Anim. Sci. 51 (suppl. 1), p. 266, Abstract 390.
Kohler et al., (1975), Nature 256:495–497.

*Primary Examiner*—Christine M. Nucker
*Attorney, Agent, or Firm*—Wegner & Bretschneider

[57] ABSTRACT

An isolated, substantially pure bovine pregnancy antigen for detecting and determining pregnancy in cattle consisting of a glycoprotein obtained from a pregnant bovine animal which is characterized by having a specific immunological reaction with a monoclonal antibody directed specifically against said glycoprotein wherein said monoclonal antibody is produced from hybridoma ATCC HB 8846.

4 Claims, 2 Drawing Sheets

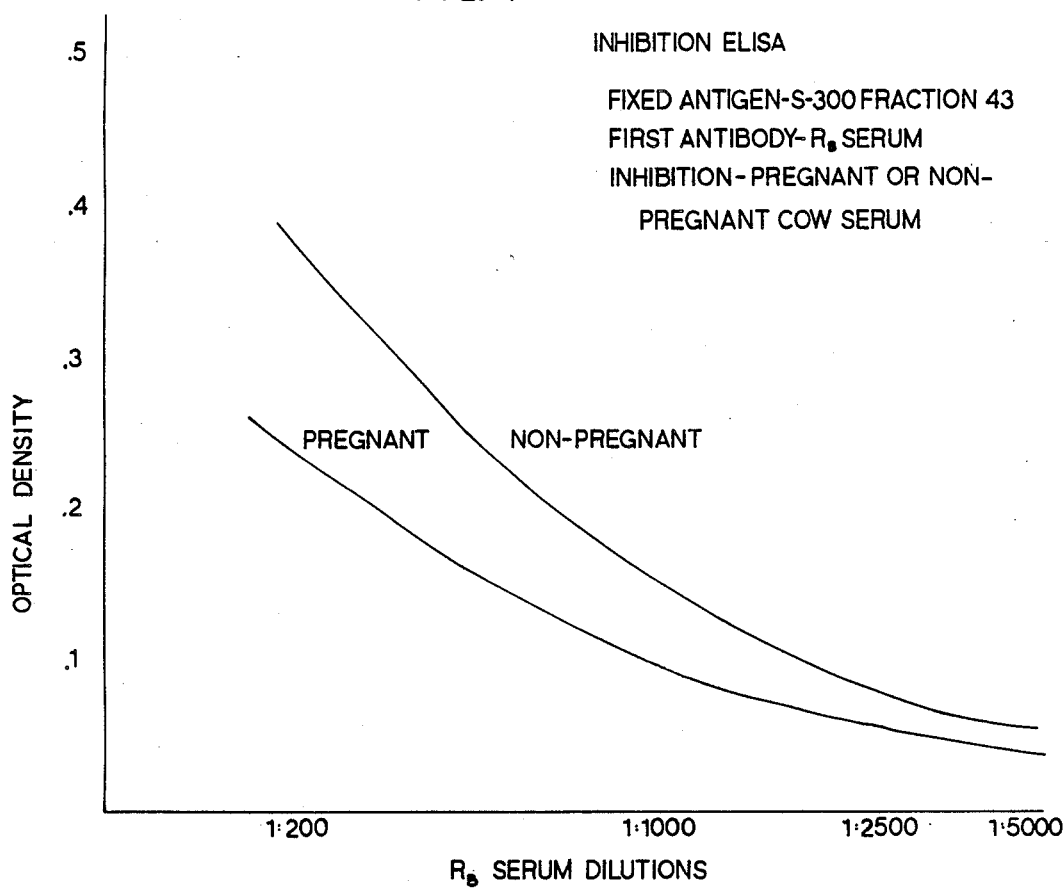

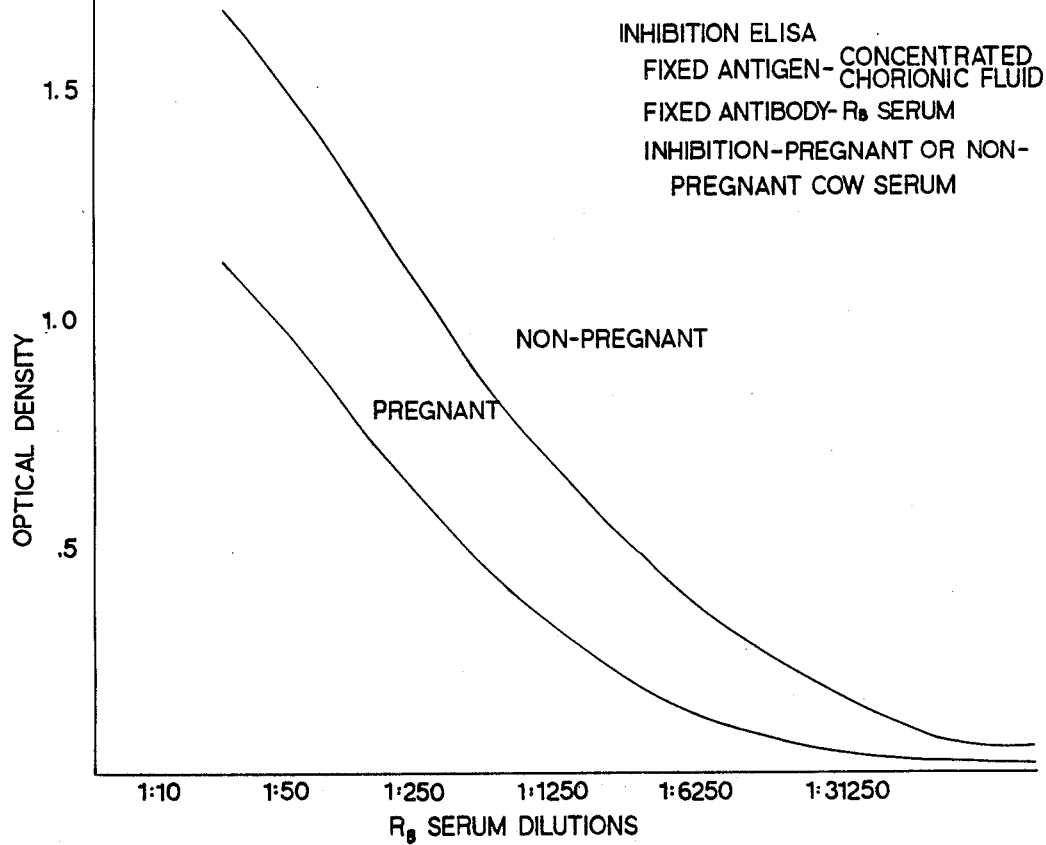

BOVINE ANTIGEN GLYCOPROTEIN, RELATED ANTIBODY, AND USE IN DETECTION OF PREGNANCY IN CATTLE

This application is a continuation-in-part of U.S. application 628,571 (filed July 6, 1984, now U.S. Pat. No. 4,755,640) and is a continuation-in-part of U.S. application 752,510 (filed July 8, 1985, now abandoned) These parent applications are hereby incorporated by reference.

This invention relates to a bovine pregnancy antigen, to a process for isolating it, to its use to create a diagnostic assay for the detection and supervision of pregnancy in cattle, and to an antibody related to the bovine pregnancy antigen.

BACKGROUND OF THE INVENTION

Detection of pregnancy in cattle, especially dairy cattle, is of great economic importance. Production of the hormone moiety required for milk production depends on a routine regimen of pregnancy for each cow. Toward this goal, and for a number of other reasons, 70% of the dairy cows in the U.S. are artificially inseminated. Conception can only occur if insemination occurs at the proper stage of the estrous cycle of the cow. Since this receptive phase of the estrous cycle lasts only a relatively short time, an unsuccessfully bred cow can not be reinseminated until estrus (heat) occurs in the following cycle (21 days later). An important objective of the dairy industry, therefore, is to detect those animals in which a successful pregnancy was not established so that they may be rebred at the next cycle. If detection occurs before the first cycle is complete, the cow can be reinseminated in the next heat, about 21 days after the first attempt. If detection is not possible in that time reinsemination must wait until the second cycle, 42 days after the initial insemination or the third cycle at 63 days. The economic impact of having non-pregnant cattle for these extended periods of time can be substantial.

Presently, the majority of pregnancy detection in cattle is performed by veterinarians. The method used is a rectal palpation where the vet physically feels the presence of a developing fetus by "slipping" or manipulating the membranes of the placenta. This technique only becomes effective, however, in the period between 30 and 42 days of pregnancy. Depending on where in that time interval detection is made, at least one, and perhaps two cycles could be missed. There are other problems with the rectal palpation method: first, the vet has to be present at the farm; and second, while the data are inconclusive, it has been reported that there is a perception on the part of some farmers that the mechanical manipulation required with rectal palpation might increase the risk of spontaneous abortion.

Another method of pregnancy detection is the assay of progesterone in milk. Progesterone is a steroid which is necessary for normal development and maintenance of pregnancy. Serum titers of progesterone rise throughout early stages of pregnancy, and increased levels of the hormone are found in milk. A radioimmunoassay (RIA) can detect the increase in milk progesterone. This technique has a number of shortcomings. By definition, an RIA requires the use of radioactive material. Inherent in this requirement are several disadvantages, including the need for sophisticated laboratory equipment, preventing both the farmer and most veterinarians from performing the test. In addition, the level of progesterone varies both between normal non-pregnant cows and within individual cows throughout the estrous cycle. Therefore, baseline readings for each cow are necessary, and at least two determinations are required to confirm pregnancy. Furthermore, this method is reported to be unreliable earlier than 20 days after insemination.

It is clear that a more simple, rapid and accurate means of detecting pregnancy in cattle would be of great value.

The present inventors have reported, J. Animal Science, 57, Supp. 1, 320 (1983), the initial isolation and partial characterization of protein specific to the chorionic membrane of bovine embryos. This protein was reported to be a high molecular weight compound which, at one point in the isolation process, appeared to stain as a glycoprotein. However, this protein had not been fully structurally characterized or sufficiently purified to be utilized for practical purposes. Furthermore, it had not been reported or suggested that such a protein would be found in the body components of the mother or would be diagnostic for pregnancy, or provide the basis for a pregnancy assay.

It has not been hitherto known that a bovine pregnancy antigen can be isolated from the embryo or body components of pregnant cattle, or that such an antigen could serve as the basis for a diagnostic pregnancy assay.

OBJECTS OF THE INVENTION

An object of the present invention is a process for isolating a bovine pregnancy antigen by fractionation from the embryo or body components of pregnant cattle. Another object of the present invention is the bovine pregnancy antigen itself. Yet another object of the present invention is an antibody specific to the bovine pregnancy antigen.

A further object of the present invention is a diagnostic assay for the detection and supervision of a bovine pregnancy, which contains as an essential diagnostic component the bovine pregnancy antigen and/or antibody specific for the bovine pregnancy antigen.

GENERAL DESCRIPTION OF IMMUNOCHEMICAL REACTION TECHNIQUES

In general, the production of antibodies to a substance and the use of the antibodies in assays for the substance is a practice well known to the art. The antibodies may be polyclonal or monoclonal, although the specificity of the monoclonal antibodies is generally advantageous and they are usually utilized when available. The present invention relates to the finding of a previously heretofore unrecognized bovine pregnancy antigen, antibodies specific thereto and the use of the latter in detecting pregnancy in cattle. The diagnostic assay of the invention may be used for either the qualitative or quantitative detection of the bovine pregnancy antigen.

SUMMARY OF THE INVENTION

The present invention relates to (1) a novel bovine pregnancy antigen indicative of pregnancy in cattle, (2) methods for the isolation, purification and characterization of the antigen, (3) the use of the antigen to provide assays useful for the early detection of pregnancy in cattle, (4) the preparation of polyclonal and monoclonal antibodies to the antigen, (5) the use of the antibodies of the invention to provide assays useful to detect the antigen, and (6) pregnancy detection kits comprising one or more components described above.

The bovine pregnancy antigen for detecting and determining pregnancy in cattle is a glycoprotein obtained from a pregnant bovine animal and is characterized by
(a) binding nicotinamide-adenine dinucleotide,
(b) having active portions with a molecular weight of about 158,000 to 263,000 daltons,
(c) containing at least the carbohydrates N-Ac-glucosamine, galactose, and L-frucose and either D-mannose or D-glucose or both,
(d) having an isoelectric point range of 4.5 to 5.5, an
(e) giving a blue stain with Coomassie Blue, and
(f) antibodies to which hemoglobin, albumin, bovine luteinizing hormone, IgG, fibrinogen, fetuin, and alpha fetoprotein are not cross-reactive.

DETAILED DESCRIPTION OF THE INVENTION

Preparation of Bovine Pregnancy Antigen

For preparing the bovine pregnancy antigen, bovine chorionic fluid was concentrated by precipitation in 50% aqueous ammonium sulfate solution. The precipitate was resuspended and desalted either by exhaustive dialysis in buffer (0.01 M Tris, 0.15 M NaCl, pH 7.5), or by passage through a Bio-gel P-2 column. An aliquot of the desalted sample was tested with saturated barium sulfate to assure that removal of ammonium sulfate was complete. Protein concentration was determined by the method of Lowry et al., J. Biol. Chem., 193, 265 (1951) or by the Bradford microassay (BioRad Laboratories, Richmond, CA). Although the following description relates to isolating the bovine pregnancy antigen from bovine chorionic fluid or the chorionic membrane, the antigen can be purified also from the maternal blood of a pregnant cow.

A sample of the ammonium sulfate-treated material was mixed with an equal volume of 2 M perchloric acid. The soluble fraction, deduced to be mostly glycoproteins by virtue of tits solubility in perchloric acid, was then dialysed against phosphate buffered sale before determining protein concentration and immunoreactivity.

The ammonium sulfate chorionic fluid preparation was applied to a Sephadex G-200 column (Pharmacia Fine Chemicals, Uppsala, Sweden). Samples were collected in 2 ml fractions and a chromatograph recorded absorbance at 280 nanometers, as the concentrated sample was eluted from the column.

Alternatively, a sample of the ammonium sulfate chorionic fluid preparation was applied to a column of Sephacryl S-300 (Pharmacia Fine Chemicals, Inc.). This acrylamide cross-linked dextran matrix facilitates the resolution of large molecular weight components (limits: 10,000 –1.5 $10^6$ daltons). Samples were again collected in 2 ml fractions and absorbance of the fractions at 280 nanometers were recorded.

The desired bovine pregnancy antigen, a glycoprotein, was found by immunoreactivity to be located primarily in a column fraction 43. This fraction 43 represented a fairly broad peak, and the maximum molecular weight was estimated to be 500,000 daltons. A more complete view of this fraction was obtained in a 3% –27% gradient SDS-polyacrylamide gel and 10% SDS polyacrylamide gel. These gels demonstrated that under reducing conditions this immunoreactive peak was composed of 3 to 4 bands, ranging in molecular weight from 220,000 to 600,000 daltons. Subsequent analysis showed active portions of the antigen at molecular weights of about 158,000 to 263,000 daltons; see Example 15 infra.

Electrophoretic techniques were employed to more fully understand the nature of the bovine pregnancy antigen. Native and denaturing SDS-polyacrylamide gels with T values of 8%, 10%, 12%, and 3%–27% gradient were run and the gels were stained with either Coomassie Blue or silver stain by methods known to the art.

Electrophoretic patterns of fraction 43 revealed 3 to 4 bands. These included a doublet around 220,000, a large, illdefined band around 400,000 and one or more bands which contain material with a molecular weight too large to enter the 10% gel. These latter bands appeared in the uppermost regions of the 3%27% gel. The doublet at 220,000 closely resembled the pattern of fibrinectin when treated under similar conditions. The large component at 400,000 resembled a glycoprotein in its staining behavior with Coomassie Blue. This component has also been found to bind to nicotinamide-adenine dinucleotide (NAD), which is characteristic of a glycoprotein.

It has been determined that the portion of the chorionic fluid which reacts with antibodies must correspond to the 400,000 dalton component of fraction 43. The bovine pregnancy antigen is a glycoprotein and preliminary isoelectric focusing studies indicate the protein is acidic.

The bovine pregnancy antigen can be readily detected in pooled blood sera from superovulated cows 13 days pregnant.

Preparation of Polyclonal Antibodies

Polyclonal antibodies to the bovine pregnancy antigen were prepared as follows: Rabbits were immunized against CCF using standard methods as described in more detail in the Examples. After immunization was complete, rabbit serum which was determined to react with the marker bovine pregnancy antigen was collected on a regular basis and stored for later use.

Preparation of Monoclonal Antibodies

Monoclonal antibodies to the marker bovine pregnancy antigen were prepared as follows:

Step 1. Preparation of a Monoclonal Antibody

The monoclonal antibodies useful in the present invention are obtained by a process similar to that discussed by Milstein and Kohler and reported in Nature, 256:495–497, 1975. The details of this process are well known in the art and will not be repeated here. However, what is involved is injecting a mouse (or other suitable animal) with immunogenic material. In the present invention, that material is a partially or completely purified glycoprotein. The immunized animals are sacrificed and cells from their spleens are fused, e.g., with mouse myeloma cells.

The result is a hybrid cell, known as a "hybridoma", that is capable of reproducing in vitro. The population of hybridomas is then screened for immunoglobulin production. Any of the several known methods for screening for immunoglobulins such as those described in U.S. Pat. No. 4,016,043 may be used. The enzyme-linked immunosorbent assay method described in U.S. Pat. No. 4,016,043, using commercially available reagents from several sources (such as Cappel Company)

was found to be conveniently applicable. The immunoglobulins present in the cell culture fluids were further examined for their ability to react with the glycoprotein (bovine pregnancy antigen) used for immunization. This can be accomplished by modifications of the above-mentioned enzyme immunoassay.

Step 2. Identify Cell Clone

A specific clone producing the identified antibody, e.g., antibodies to the bovine pregnancy antigen, can be propagated by maintaining it in a suitable medium and at a suitable temperature. A representative example is the use of Dulbecco's minimum essential medium (DME) in the presence of 10% carbon dioxide and 10% fetal calf serum at 37° C.

Step 3. Antibody Isolation

The proteins, i.e., antibodies used in the assay, are obtained by treating the tissue culture fluids from the spleen cell-myeloma cell fusion describe above with 50% ammonium sulfate. This treatment resulted in the precipitation of the desired antibodies. The precipitate is optionally (and preferably) resuspended in a buffered saline solution for further use.

Step 4. Antibody Immobilization

The antibodies obtained to the bovine pregnancy antigen are identified, propagated, isolated as above and then used, e.g., by immobilization or in solution. For example, antibodies may be absorbed onto various water insoluble matrices such as microtiter plates, Dextran beads, nylon web, glass, cellulose, polyacrylamide, charcoal, urethane, ceramic, or mixtures thereof.

The antibody may be bound to the matrix by various methods known to the art, for example chemically, i.e., by the formation of ionic or covalent bonds or physically, i.e., by absorption, entrapment in an insoluble matrix, and the like.

The bound antibody can then be provided in a kit wherein body fluids from female bovine animals would be added and activity of the antibody with the fluids could be measured.

Description of the Drawings

FIGS. 1 and 2 are plots of optical density against serum dilutions (dilution curves) for determining pregnancy in cattle using the techniques of the present invention. They are discussed in Examples 10 and 14, infra.

The following examples are representative of the invention.

EXAMPLE 1

Collection of Embryonic Tissues and Fluids

The reproductive tracts of 355 pregnant cattle were obtained from a local abattoir immediately after slaughter of the animals and returned to the laboratory as quickly as possible. To reduce the possibility of sample cross-contamination, tissues were collected in the following order. First, the uterus was carefully sliced open and the cotyledon/caruncle interdigitations gently pulled apart to allow the intact placenta to fall away free. Using a 21 gauge needle and a 15 ml syringe, a 12 ml sample of chorionic fluid was withdrawn and the fluid stored at $-20°$ C. until needed. Similarly, other fluids were sampled and other tissued preserved.

EXAMPLE 2

Collection of Adult Bovine Samples

Bovine blood serum was collected by jugular venous puncture, allowed to clot overnight at 4° C., and then centrifuged at 1000 x g for 15 minutes. Serum was drawn off with a disposable pipette, pooled (at least 6 animals per sample), and stored at $-20°$ C.

EXAMPLE 3

Tissue Homogenates

Pooled samples (at least 10 specimens) of chorion, from Day 45 of gestation were weighed, minced, and suspended in 20% weight/volume cold phosphate-buffered saline (PBS). Each preparation was homogenized for 2 minutes (30 second bursts) in a Brinkman Polytron Tissue Homogenizer (Brinkman Instruments, Inc., Westbury, N.Y.). An ice pack was maintained around each tissue container during homogenization.

EXAMPLE 4

Embryonic Fluids

Chorionic fluid samples were pooled and then concentrated to approximately 1 mg protein/ml by the addition of Lyphogel (Gelman Instrument Company, Ann Arbor, MI) to each dilute solution. Lyphogel is a dry, selectively absorbent polyacrylamide material which absorbs a precise multiple of its own weight in water, salt, and other small molecules (rejection limit 20,000 MW) from aqueous solution. The pH and osmolarity were unaffected. After the desired amount of water absorption, the Lyphogel was removed from each sample by suction filtration.

Alternatively, small chorionic fluid samples were concentrated using an Amicon B15 clinical sample concentrator (Amicon Corp., Lexington, MA). This disposable multiple ultrafilter concentrates macromolecular constituents of dilute samples at a rejection limit of 15,000 MW.

Pooled, concentrated chorionic fluid samples from day 65–75 of gestation were used for isolation of the bovine pregnancy antigen. Samples were first pooled and then concentrated 25-fold for chromatography.

EXAMPLE 5

Preparation of Antisera

Two mature New Zealand white rabbits (female) were immunized against each of the Day 45 of gestation tissue or fluid samples described in Examples 3 and 4 above. Equal volumes of tissue homogenate or concentrated extraembryonic fluid were emulsified with Freund's adjuvant (Difco Laboratories, In., Detroit, MI). Each rabbit was injected intradermally with 1.0 ml of the emulsion at multiple sites over the scapular region. The initial injection employed Freund's complete adjuvant, composed of Arlacel A (mannide mono-oleate), Bayol F (paraffin oil), and *Mycobacterium butyrium*. All other injections included incomplete adjuvant which did not contain the bacteria. The second injection was administered one week later and three booster injections were given at two weeks intervals.

Normal serum was obtained from each rabbit prior to injection. A pool of normal rabbit control serum consisted of blood from at least three animals. Rabbit sera were collected three days prior to the third immunization and at weekly intervals thereafter. Rabbits were bled from the marginal ear vein. The blood was allowed to clot overnight at 4° C., and then centrifuged for 15 minutes at 1000 xg. Serum was removed with a disposable pipette and stored at $-20°$ C. until used.

EXAMPLE 6

Ammonium Sulfate Fractionation

Salting out with ammonium sulfate was performed (in a 4° C. room) at 33, 50, 66, 80, and 100% saturation on fractions of pooled, concentrated chorionic fluid from Days 65-76 of gestation (see Example 4).

Cold ammonium sulfate was added in a dropwise manner with continuous mixing. Samples were stirred for 2 minutes and then centrifuged at 4° C. for 10 minutes at 12,000 xg. The supernatant fluid was removed and the precipitate redissolved in 0.005 M PBS to the original sample volume. All fractions were examined for absorbency at 278 nm on a Beckman Model 25 double-beam spectrophotometer (Beckman Instruments, Inc., Fullerton, CA). Ouchterlony analysis determined which fraction reacted most strongly with the rabbit antisera against chorionic fluid proteins.

EXAMPLE 7

Sephadex G-200 Chromatography

Protins in bovine chorionic fluid from Days 65-75 of pregnancy were separated by column chromatography using Sephadex gel. Sephadex swells in aqueous solutions given a porous gel. Only molecules below a certain size (exclusion limit) can enter the pores, while larger molecules must pass through the column in the liquid phase outside the gel particles. These large molecules elute first. Smaller molecules penetrate the pores to varying degrees, dependent on their shape and size. Elution through Sephadex columns, therefore, occurs in order of decreasing molecular weights. The gel and column were prepared as described by Okonkwo (1981):

1. Seven grams of Sephadex G-200 (PHarmacia Fine Chemicals, Upsala, Sweden) were suspended in 0.005 M PBS pH 7.4. The dry gel was allowed to swell in excess buffer with intermittent stirring and decantation for 24 hours at 4° C.

2. A 25×65 cm column (LKB 2137, Bromma, Sweden) with two flow adaptors was used.

3. The column was filled with buffer to a higher of 5-10 cm. The swollen gel, which was suspended in a volume of buffer approximately twice the expected bed volume, was carefully poured into the reservoir and air bubbles were removed. Flow rate was adjusted to 15 ml per hour as recommended for Sephadex G-200. The bed was stabilized by eluting with approximatley two bed volumes of eluent.

4. Standards (Pharmacia) were used for calibration of the column. The protein standards used were

| Protein Std. | Mol. Wt. | Source |
| --- | --- | --- |
| Aldolase | 158,000 | Rabbit Muscle |
| Ovalbumin | 45,000 | Egg White |
| Cytochrome C | 27,270 | Horse Heart |

5. The column was loaded with a 2 ml sample of concentrated chorionic fluid from Days 65-75 of gestation, containing about 20 mg of protein, and was eluted with 250 ml of buffer. Five ml fractions were collected at a rate of 15 ml/hr with a fraction collector. All fractions were examined for absorbency at 278 nm.

EXAMPLE 8

Monoclonal Antibody Production

1. Fusion a. Mice (Balb/c) were immunized i.p. with the rechromatographed 50% ammonium sulfate precipitate fraction of chorionic fluid (see Example 7) at weekly intervals. Three days after their final injection, the spleens were aseptically removed from the immunized animals and placed in culture medium (Dulbecco's modified Eagle's medium with Hepes buffer (20 mm), (Gibco Laboratories, Grand Island, N.Y.) with double antibiotics (200 mM L-glutamine and 50 mg/ml Gentamycin). Serum was also collected at this time and stored at −20° C. for future use.

b. Spleens were washed in sequential petri dish baths (2× ) of culture medium and then placed in a final dish containing 10 ml of the medium for pulp removal. Clear, empty spleen cases were then discarded and the pulp and medium transferred to 15 ml conical bottom sterile plastic test tubes (Corning Glassworkd, Corning, N.Y.).

c. Tubes were centrifuged at 120 ×g for 3 min., the supernatant fluid removed, and the pellet resuspended in 10 ml of fresh culture medium. Viable cells were counted by Trypan Blue exclusion. Spleen cells were diluted to $1 \times 10^8$ cells and distributed into 16 ×125 mm plastic round bottom tubes (Corning Glassworks, Corning, N.Y.).

d. NS-1 plasmacytoma cells in log growth phase at 90% or greater viability were added to the tubes containing the spleen cells at a concentration of $2.5 \times 10^7$ NS-1 cells, and the tubes centrifuged at 120 ×g for 3 min.

e. The supernatant fluid was removed from all tubes by suction. The tubes were then tapped to break up the pellets and 1 ml of polyethylene glycol (PEG) solution was added. This marked the start of PEG exposure timing. Tubes were shaken gently to resuspend all cells in the PEG and then were recentrifuged at 120 ×g for 5 min. Tubes were next removed to the laminar flow hood (Labgard, NuAire, Inc., Plymouth, MN) and allowed to incubate for about 3 min. longer (Total PEG exposure equals 8 min.).

f. PEG was quickly removed by suction and 10 ml of the culture medium added to each tube without disturbing the pellet. Tubes were recentrifuged at 120 ×g for 3 min. The supernatant fluid was again removed by suction.

g. Tubes were tapped gently to break up the pellets and 10 ml of culture medium with antibiotics and serum (500 ml Dulbecco's modified Eagle's medium with Hepes buffer (Gibco), 50 ml heat-inactivated fetal calf serum (Gibco), 5 ml L-glutamine, and 0.5 ml gentamycin slowly added. While the tubes were allowed to sit, an additional 10 ml of this medium for each tubes was added to a 150 cm² flask. The contents of all tubes were then poured into the flask and the cells were allowed to recover overnight at 37° C.

h. The following morning, cell viability was again determined and the cells redistributed at a concentration of $10^6$/ml in HAT selection medium. This cell suspension was then pipetted (0.3 ml/well) into the inner 60 wells of a 96-well culture dish (Costar, Cambridge, MA). The outer wells were filled with sterile water and the plates were sealed and placed in a 37° C.

incubator (Forma Scientific 3916, Mallinckrodt, Inc., Marietta, OH) in large plastic bags.

i. Three days later, fresh HAT selection medium was added. Henceforth, cultures were observed daily and the medium changed as required. Hybrids appeared 10-14 days after fusion and were expanded into larger culture dishes as needed.

2. Feeder Plates

Cells in culture do not survive well when their numbers are reduced below some critical level. Feeder plates provide environmental conditions conducive to hybridoma growth from single cell dilutions. Feeder spleen cells are not immortal and die off in about two weeks.

a. Spleens were aseptically removed from non-immunized animals, washed, the pump removed, cells centrifuged, resuspended, and viability determined as described above. Cell density was adjusted to $10^6$ cells/ml and the suspensions were placed in a 150 cm$^2$ flask overnight at 37° C.

b. The unattached cells were gently resuspended and removed from the flask the following morning, centrifuged and resuspended at $5 \times 10^6$ viable cells/ml.

c. This suspension was then rapidly pipetted (0.1 ml/well) into the inner 60 wells of a 96-well plate. The outside wells were again filled with sterile water. These plates were then ready for either expansion or subcloning use.

EXAMPLE 9

1. Expansion

To reduce the possibility of cross-contamination between wells with repeated feedings, and to encourage colony growth, cells were moved to new and/or larger welled plates as needed. At that time supernatant fluids can be readily harvested for testing.

a. Cells in the fusion plate wells were resuspended using a sterile transfer pipette and half of the suspension was removed to a 15 ml round bottom tube. Six ml of HAT selection medium were added and the cells redistributed to the inner 60 wells of a feeder plate.

b. Cells were fed fresh culture medium every second day and observed until hybrid colonies were 60-80% confluent. Supernatant fluid from each well was then tested for immunoglobulin production by ELISA techniques as described in Example 10, infra.

c. The following day, supernatant fluid and cells were collected and pooled from all positive wells. Suspension were centrifuged (5 min. at 120 x g), the supernatant fluid was removed and saved, and the cells resuspended in fresh medium with antibiotics and either expanded and subcloned, or frozen as safety stocks.

2. Subcloning

Each original fusion plate has the potential to produce hundreds of hybridoma cells capable of secreting an antibody of interest. To achieve monoclonal antibody production, these cells must eventually be plated one to a well and allowed to grow. These pure clones are the desired end product of cell fusion.

a. Using cells from the expansion plate, a 1 ml suspension containing $10^6$ cells in fresh culture medium in a plastic 15 ml round bottom tube (Corning Glassworks) was made up.

b. Nine ml of this medium were added and the tube inverted several times to mix (not $10^5$ cells/ml).

c. Next, 0.1 ml was removed and added to 9.9 ml of the same medium in a new tube and mixed ($10^3$ cells/ml).

d. Finally, 0.2 ml was removed and added to 30 ml of the medium in a new tube (5-7 cells/ml), mixed and distributed to feeder plates at 0.1 ml/well. Final plating density about 0.6 cells/well.

e. Plates were refed in 2-3 days and observed daily until they reached 60-80% confluency. Supernatant fluids were again tested for immunoglobulin production.

EXAMPLE 10

Enzyme-Linked Immunosorbant Assay (Elisa)

ELISA utilizes enzyme-linked (second) antibodies for which visulaization can be provided by a measurable color change. Use of a supported antigen increases the ease of handling, while environmental risks, such as radiation exposure, are eliminated. ELISA methodologies are excellent for the rapid, large scale screening required when working with hybridomas.

a. Costar 1/2 area microtiter plates were coated overnight at 4° C. with 50 ul/well of the same bovine pregnancy antigen preparation used to immunize the mice diluted in carbonate buffer (1.59 g Na$_2$CO$_3$, 2.93 g NaHCO$_3$ and 0.2 g NaN$_3$ per liter distilled water, pH 9.6).

b. Before use, plates were washed thrice with PBS-Tween and flicked dry.

c. Antibody solution (50 ul) was added to each well and allowed to incubate at room temperature for 1 hr.

d. Plates were again washed thrice and flicked dry.

e. Next, 50 ul of peroxidase-conjugated Protein A which normally bonds to IgG (Kirkgaard and Perry Laboratories, Inc., Gaithersburg, MA), diluted 1:5000 in PGS-Tween (8.0 g NaCl, 0.2 g KH$_2$PO$_4$, 2.9 g Na$_2$HPO$_4$, 12 H$_2$O, 0.2 g KCl, 0.5 ml Tween 20, per liter distilled water, pH 7.4), was added to each well and allowed to incubate 1 hour at room temperature.

f. Again plates were washed thrice with PBS-Tween and flicked dry.

g. Substrate (20 ml Citrate buffer, 10 mg o-phenylenediamine, 10 ul H$_2$O$_2$ immediately before use) was added (50 ul/well) and color allowed to develop for 15-30 min.

h. Plates were read on Dynatech MR580 Microelisa Reader (Dynatech Laboratories, Inc., Alexandria, VA).

Results are portrayed as dilution curves as shown in FIGS. 1 and 2, and explained in Example 14, infra.

EXAMPLE 11

Serum samples were obtained prior to artificial insemination of each cow, and again 12 to 15 days post-insemination. Pregnancy was determined by rectal palpation after all samples had been collected. The results of analysis of the samples are shown in Table I. Several monoclonal antibodies were tested for each serum sample from each cow. The designations D14B001 A2, D14B002 A3, D15B003 A3, and D15B003 A4 are all monoclonal antibodies raised against the bovine pregnancy antigen. A representative hybridoma cell line that produces monoclonal antibodies in accordance with the present invention is ATCC HB 8846.

TABLE I

| Serum Sample Number | Antibody | % Inhibition by Post Insemination Sample |
| --- | --- | --- |
| 1 | Polyclonal | 45 |

TABLE I-continued

| Serum Sample Number | Antibody | % Inhibition by Post Insemination Sample |
|---|---|---|
| | Antiserum | |
| 1 | D14B001 A2 | 21 |
| 1 | D14B001 A4 | 39 |
| 1 | D15B003 A3 | 27 |
| 1 | D15B003 A4 | 16 |
| | | x = 29.6, s = 12.1 |
| 2 | D14B001 A2 | 53 |
| 2 | D14B001 A4 | 31 |
| 2 | D14B002 A3 | 22 |
| 2 | D15B003 A3 | 46 |
| 2 | D15B003 A4 | 17 |
| | | x = 35.7, s = 18.7 |
| 3 | Polyclonal Antiserum | 48 |
| 3 | D14B001 A2 | 52 |
| 3 | D14B001 A4 | 42 |
| 3 | D14B002 A3 | 28 |
| 3 | D15B003 A3 | 32 |
| 3 | D15B003 A4 | 57 |
| | | x = 43.1, s = 11.4 |
| 4 | Polyclonal Antiserum | 16 |
| 5 | Antiserum polyclonal | 12 |

These results show that the cows that provided samples 1, 2, and 3 were pregnant. Sample 1 was 12 days pregnant, samples 2 and 3 were 15 days pregnant, and Samples 4 and 5 were provided by non-pregnant cows. The antibody was added with the serum samples to the wells which were coated with the bovine pregnancy antigen preparation. After incubation, peroxidase-labeled protein A was added. Following this reaction, color changing substrate was added and color change observed. These results demonstrate that pregnant cows can be distinguished from non-pregnant cows by the method shown.

EXAMPLE 12

A 500 ml column was filled with Sephacryl S-300 and the column was packed by running Tris buffer (0.01 M trishydroxyethylamine, 0.15 M sodium chloride, pH 7.5) through at 0.667 ml/min. The column was calibrated using standard proteins.

A 5 ml sample of concentrated chorionic fluid was obtained by precipitation of chorionic fluid with 50% ammonium sulfate, separation of the insoluble fraction, and washing and redissolving with water. The sample was then added to the column and eluted with Tris buffer. Fractions of 2.1 ml were collected and the flow rate was 0.24 ml/minute. A series of peaks were detected by optical density measurement at 280 nanometers. The molecular weight is estimated by comparison with the standards. Peaks were observed at greater than 600,000 (void volume), about 400,000, about 150,000, about 65,000, about 31,000 and about 18,000 daltons.

EXAPLE 13

The various fractions of the column run in Example 12, especially the fraction of about 400,000 daltons, were allowed to react with rabbit serum containing polyclonal antibodies to concentrated chorionic fluid containing the marker glycoprotein (see Example 5). A precipitant band was found with its apex at the 400,000 dalton peak. This result indicates that this protein is the marker protein for pregnancy in cattle.

EXAMPLE 14

Partially purified concentrated chorionic fluid (as obtained in Example 13 and described hereinabove as fraction 43) was diluted 1:100 in carbonate buffer (pH 9.6) to be fixed into microtiter plate wells.

Rabbit antiserum was diluted from 1:10 to 1:780,000. Serum was obtained from a cow prior to artificial insemination (non-pregnant) and also about 15 days after insemination (pregnant). The serum samples were assays using the method of Example 10.

It was found that the serum obtained from the pregnant cow blocked binding markedly more than the serum obtained prior to artificial insemination over the entire range of dilutions. The results are shown graphically in FIG. 1.

EXAMPLE 15

Using the general method of Example 12, but taking smaller fractions (1 ml) of the eluate, a set of samples was obtained from 500 ml of chorionic fluid clarified by centrifugation.

The set of samples contained 5 major peaks. When treated for the bovine pregnancy antigen in a counterimmuno-electrophoresis assay, all of the antigenic activity was contained in the second major peak. This major peak included the fraction designated 43 in earlier separations. The entire group of fractions corresponding to the second major peak was pooled and designated Fraction 2.

Samples of Fraction 2 were diluted with equal volumes of a buffer containing 2-mercaptoethanol. The mixture was boiled for 5 minutes, then applied to a 5 to 15% linear gradient polyacrylamide gel, and electrophoresed at 30 milliamps for 2 to 3 hours. The gels were then either fixed and stained for protein (to assess molecular weight) or placed in tris-glycine-methanol buffer and transferred by electrophoresis tonitrocellulose paper (transblots). The transblots could be stained for protein detection or reacted with various antibodies.

Although the molecular weights as determined by this method are more precise, i.e., peaks at 158,500 daltons (major), 208,900 daltons (secondary) and 263,000 daltons (tertiary), they may possibly represent partial degradation of the antigen glycoprotein. Each of these peaks retains significant antigenic activity and thus represent major constituents or the only major constituent of the antigen.

EXAMPLE 16

A sample of Fraction 2 of Example 15 was evaluated by isoelectric focusing on both agarose and polyacrylamide gels.

Using a 3.5 to 9.5 pH gradient on polyacrylamide gel, bands were found at 4.7, 5.3, 5,45 to 5.8, and 6.6 to 6.75.

Using a 3 to 10 pH gradient on agarose gel, bands were found at 4.5, 5.3 (a doublet), and 5.5. Therefore, the band or bands attributable to the glycoprotein antigen are in the range 4.5 to 5.5.

The reference pH values are determined using a surface electrode; glycoprotein bands are located on the fixed gel stained with Coomassie Blue dyes.

EXAMPLE 17

Lectins are a group of plant protins that specifically bind to sugars or their derivatives. Since the bovine pregnancy antigen is a glycoprotein, a purification shceme based on differential binding to immobilized lectins was possible.

Two types of survey experiments were performed, batch-wise and column fractionation of the active chorionic antigen fraction. All experiments were performed in 10 mM Tris, 150 mM NaCl, and 0.002% NaN$_3$ buffer. In the batch experiments 100 ul of washed resin (immobilized lectin) were rocked with 150 ul of the test solution for 135 min. at ambient temperature. the supernatants were saved for antigen analysis. These fractions contained unbound protein. The resin was washed 4X with the buffer, then rocked for 1 hr. with the corresponding sugar. The supernatant from this fraction was also saved for analysis, comprising those proteins which were specifically bound to lectin.

The column fractionation was similar to the batch experiment. A small column of resin was prepared in buffer. Three ml of test solution were loaded onto the column followed by a buffer wash. Elution with the specific sugar in buffer followed by 1% SDS (sodium dodecylsulfate, a denaturing detergent) in buffer was then carried out. These fractions were analyzed for antigen activity.

The results of the column experiments reproduce the batch results and gave enough material for SDS-PAGE analysis. Separate ConA columns were elute with either α-methylmannoside or α-methylglucoside and yielded identical results. No antigen passed through the column; sugar eluted antigen as did SDS.

In the T. purpureas column experiment, antigen eluted in the loading/washing, sugar, and SDS fractions. Identical behavior was seen with the WGA column.

Conclusion: The bovine pregnancy antigen contains the following sugars: N-Ac-glucosamine, galactose, L-fucose, and either D-mannose or D-glucose or both.

| Lectin | Sugar |
| --- | --- |
| Concanavalin A (ConA) | α-methylmannoside |
|  | α-methylglucoside |
| Lentil | α-methylmannoside |
|  | α-methylglucoside |
| T. purpureas | L-fucose |
| Ricinis communis II ($M_r$ = 120K) (RCA) | galactose |
| Wheat germ (WGA) | N—Ac-glucosamine |

We claim:

1. An isolated, substantially pure bovine pregnancy antigen for detecting and determining pregnancy in cattle consisting of a glycoprotein obtained from a pregnant bovine animal which is character ized by having a specific immunological reaction with a monoclonal antibody directed specifically against said glycoprotein wherein said monoclonal antibody is produced from hybridoma ATCC HB 8846.

2. A hybridoma comprising ATCC HB 8846.

3. A monoclonal antibody produced by a hybridoma wherein said hybridoma is ATCC HB 8846.

4. A test kit to be used for the detection and determination of pregnancy in cattle comprising:
   (a) a monoclonal antibody produced from hybridoma ATCC HB 8846,
   (b) peroxidase-labeled protein A, and
   (c) color changing substrate.

* * * * *